(12) United States Patent
Champ et al.

(10) Patent No.: US 8,802,887 B2
(45) Date of Patent: Aug. 12, 2014

(54) METHOD FOR THE CRYSTALLIZATION OF 2-(4-N,N-DIETHYL AMINO-2-HYDROXY BENZOYL)-BENZOIC ACID-N-HEXYL ESTER

(75) Inventors: Samantha Champ, Ludwigshafen (DE); Manfred Hetterich, Rödersheim-Gronau (DE); Günther Gottwald, Mannheim (DE)

(73) Assignee: BASF SE (DE)

( * ) Notice: Subject to any disclaimer, the term of this patent is extended or adjusted under 35 U.S.C. 154(b) by 308 days.

(21) Appl. No.: 12/598,227

(22) PCT Filed: Apr. 17, 2008

(86) PCT No.: PCT/EP2008/054645
§ 371 (c)(1),
(2), (4) Date: Oct. 30, 2009

(87) PCT Pub. No.: WO2008/135360
PCT Pub. Date: Nov. 13, 2008

(65) Prior Publication Data
US 2010/0137629 A1    Jun. 3, 2010

(30) Foreign Application Priority Data
May 2, 2007    (EP) .................................... 07107342

(51) Int. Cl.
*C07C 69/76*    (2006.01)

(52) U.S. Cl.
USPC .......................................................... 560/57

(58) Field of Classification Search
CPC ........ C07C 67/343; C07C 49/80; C07C 69/76
See application file for complete search history.

(56) References Cited

U.S. PATENT DOCUMENTS

| | | | |
|---|---|---|---|
| 3,621,664 A * | 11/1971 | Saxer .............................. 62/542 |
| 5,670,606 A * | 9/1997 | Stouffer et al. ............... 528/272 |
| 6,409,995 B1 | 6/2002 | Habeck et al. |
| 2005/0165099 A1 | 7/2005 | Heidenfelder et al. |
| 2006/0246018 A1 * | 11/2006 | Andre et al. .................... 424/59 |
| 2007/0031352 A1 | 2/2007 | Goedel et al. |

FOREIGN PATENT DOCUMENTS

| DE | 3318652 | * 11/1984 |
|---|---|---|
| EP | 1046391 A2 | 10/2000 |
| WO | WO-03/097578 A1 | 11/2003 |
| WO | WO-2005/025529 A1 | 3/2005 |

OTHER PUBLICATIONS

Hommel et al. (DE 3318652, the English Machine Translation).*
Hommel et al. (DE 3318652, English Abstract).*
Langhals et al. "Sonnenstrahlung, Hautreaktionen und Sonnenschutz". Chem. Unserer Zeit, 2004, vol. 38, pp. 98-112.

* cited by examiner

*Primary Examiner* — Rosalynd Keys
*Assistant Examiner* — Jennifer C Sawyer
(74) *Attorney, Agent, or Firm* — Drinker Biddle & Reath LLP

(57) ABSTRACT

The present invention relates to a method for the crystallization of n-hexyl 2-(4-N,N-diethylamino-2-hydroxybenzoyl) benzoate, to a method for the production of pourable or flowable particles of crystalline n-hexyl 2-(4-N,N-diethylamino-2-hydroxybenzoyl)benzoate and to specific pourable or flowable particles of crystalline n-hexyl 2-(4-N,N-diethylamino-2-hydroxybenzoyl)benzoate.

16 Claims, No Drawings

METHOD FOR THE CRYSTALLIZATION OF 2-(4-N,N-DIETHYL AMINO-2-HYDROXY BENZOYL)-BENZOIC ACID-N-HEXYL ESTER

CROSS-REFERENCE TO RELATED APPLICATIONS

This application is a national stage application (under 35 U.S.C. §371) of PCT/EP2008/054645, filed Apr. 17, 2008, which claims benefit of European application 07107342.3, filed May 2, 2007.

BACKGROUND OF THE INVENTION

The present invention relates to a method for the crystallization of n-hexyl 2-(4-N,N-diethylamino-2-hydroxybenzoyl)benzoate, to a method for the production of pourable or flowable particles of crystalline n-hexyl 2-(4-N,N-diethylamino-2-hydroxybenzoyl)benzoate and to specific pourable or flowable particles of crystalline n-hexyl 2-(4-N,N-diethylamino-2-hydroxybenzoyl)benzoate.

The effects of sunlight, in particular of UV-B and of UV-A radiation, on the human skin and the skin reactions resulting therefrom, and the options for protecting the skin are for the most part already known and are further investigated in detail (Chemie in unserer Zeit, 2004, 38, 98-112).

Whereas UV-B radiation (290-320 nm) in particular is responsible for the formation of sunburn, UV-A radiation leads to so-called premature skin aging as a result of damage to the collagen and elastin fibers. Furthermore, UV-A radiation is able to damage DNA, which in the worst case scenario can lead to skin cancer.

The industry therefore supplies both so-called UV-B filters and UV-A filters in order to reduce the harmful effects of solar radiation on the human skin.

EP-A-1 046 391 describes the use of amino-substituted hydroxybenzophenones as photostable UV-A filters in cosmetic preparations.

WO 03/097578 describes a method for the production of n-hexyl 2-(4-N,N-diethylamino-2-hydroxybenzoyl)benzoate of the formula I

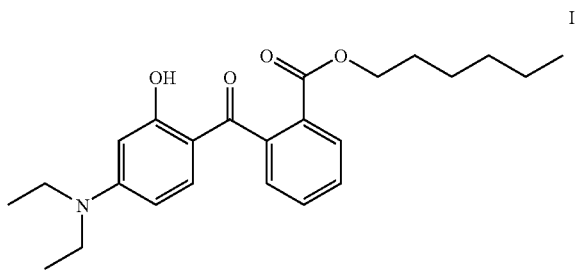 [SMILES: CCCCCCOC(=O)c1ccccc1C(=O)c1ccc(N(CC)CC)cc1O]

where the pink-colored crude product produced in the synthesis in crystalline form from solution is firstly purified by chromatography and then freed from the solvents present by distillation. Finally, the clean end product is bottled as melt.

n-Hexyl 2-(4-N,N-diethylamino-2-hydroxybenzoyl)benzoate is marketed commercially by BASF Aktiengesellschaft under the trade name Uvinul® A Plus as UV-A filter. Since the product is bottled as melt and first crystal growth occurs after storage for about six weeks at room temperature, the user has to heat the entire pack to a temperature above the melting point of n-hexyl 2-(4-N,N-diethylamino-2-hydroxybenzoyl) benzoate in order then to be able to remove liquid product from the pack.

WO 2005/025529 describes a pulverulent preparation of n-hexyl 2-(4-N,N-diethylamino-2-hydroxybenzoyl)benzoate (Uvinul® A Plus), where the UV-A filter is embedded in modified starch as protective colloid. The dry powder can be redispersed again in water, in which case the UV-A filter is present in colloidally disperse form. The protective colloid has to be tolerated in subsequent applications.

BRIEF SUMMARY OF THE INVENTION

It was an object of the present invention to provide a simple and cost-effective method for the crystallization of n-hexyl 2-(4-N,N-diethylamino-2-hydroxybenzoyl)benzoate, as well an efficient method for the production of pourable or flowable particles of crystalline n-hexyl 2-(4-N,N-diethylamino-2-hydroxybenzoyl)benzoate. Furthermore, the aim was to provide a form of crystalline n-hexyl 2-(4-N,N-diethylamino-2-hydroxybenzoyl)benzoate which is safe and easy to handle by the processor.

This object is achieved by a method for the crystallization of n-hexyl 2-(4-N,N-diethylamino-2-hydroxybenzoyl)benzoate, comprising the process steps a) providing a clear melt of n-hexyl 2-(4-N,N-diethylamino-2-hydroxybenzoyl)benzoate at a temperature above 57° C., and b) crystallizing out n-hexyl 2-(4-N,N-diethylamino-2-hydroxybenzoyl)benzoate at a temperature below 57° C., wherein the clear melt from process step a) is stirred at a temperature below 57° C. until opacity arises, before process step b) is carried out.

DETAILED DESCRIPTION OF THE INVENTION

On account of the origin of the n-hexyl 2-(4-N,N-diethylamino-2-hydroxybenzoyl)benzoate, it may also comprise small amounts of impurities from the synthesis, such as starting materials, intermediates, by-products and/or solvents.

The content of n-hexyl 2-(4-N,N-diethylamino-2-hydroxybenzoyl)benzoate in the melt provided in process step a) is preferably at least 90% by weight, particularly preferably at least 95% by weight, in particular at least 98% by weight.

Accordingly, preference is given to a method according to the invention in which the melt of n-hexyl 2-(4-N,N-diethylamino-2-hydroxybenzoyl)benzoate in process step a) has a purity of at least 98% by weight, preferably at least 98.5% by weight, in particular at least 99% by weight.

Since n-hexyl 2-(4-N,N-diethylamino-2-hydroxybenzoyl)benzoate melts at about 57° C., it suffices in principle to subject the solid starting material to a temperature of only a little above 57° C. Usually, a clear melt is provided at a temperature of from 57 to 80° C., preferably from 58 to 65° C., in particular from 59 to 62° C.

Since the crystallization of n-hexyl 2-(4-N,N-diethylamino-2-hydroxybenzoyl)benzoate does not start spontaneously at the melting point of the compound at 57° C., as described at the start, a thermodynamically metastable melt is formed below the melting point, for example at room temperature.

In process step b) of the method according to the invention, n-hexyl 2-(4-N,N-diethylamino-2-hydroxybenzoyl)benzoate crystallizes out at a temperature below 57° C. by stirring the clear melt from process step a) at a temperature below 57° C. until opacity arises, before process step b) is carried out. Preferably, the melt produced in process step a) is stirred at a temperature between 25 and 40° C., particularly preferably at a temperature between 27 and 35° C. until opaque.

For stirring the melt below 57° C., any type of stirrer can in principle be used, such as, for example, a magnetic stirrer core, an anchor stirrer, a propeller stirrer, an oblique-blade stirrer or a disk stirrer. The size of the stirrer relative to the volume of the melt is fundamentally not decisive. Preferably, the stirrer homogenizes the entire melt during the stirring time, particularly if the melt is transferred in portions to different vessels for crystallization.

It has been established that the time until opacity arises in the melt, which is caused by the formation of crystal germs, can be reduced if the speed of the stirrer, i.e. the number of revolutions of the stirrer per time unit, is increased. In the method according to the invention, the melt is preferably stirred with a stirrer at a speed of from 100 to 600 rpm, particularly preferably at a speed of from 200 to 500 rpm.

In the method according to the invention, the melt is preferably stirred with a stirrer, in particular a propeller stirrer, which has a diameter of from 2 to 20 cm, at 200 to 500 rpm, in particular 300 to 400 rpm.

In the method according to the invention for the crystallization of n-hexyl 2-(4-N,N-diethylamino-2-hydroxybenzoyl)benzoate, process step b) is preferably carried out without stirring since the melt solidifying as a result of crystallization can in any case no longer be stirred after a certain time. Therefore, after opacity has arisen, the still liquid melt can be transferred to a desired mold, where the crystallizing out step then takes place. In principle, the geometry and the construction of the mold are insignificant. However, preference is given to using those molds for which removal of the solid, crystallized-out ester presents no difficulties. Conical molds have proven to be advantageous. The volume of the molds is in principle arbitrary and can vary, for example, from 0.1 ml to 10 l or else 5 l to 100 l. The product removed from the mold can in turn be further comminuted in suitable devices, such as, for example, a mill.

In the method according to the invention, in process step b), a plane surface can also be used as mold onto which the still liquid melt of the ester is applied as a thin layer, i.e. with a small thickness compared to the length-width expansion, preferably between 0.1 and 5 mm in thickness, in particular between 0.2 and 2 mm in thickness. Alternatively, the still liquid melt can also be portioned into small drops and be placed onto the flat surface such that so-called pastilles or prills, hemispherical structures, are formed. The diameter of the hemispheres is preferably between 0.1 and 5 mm. After the ester has crystallized out, the solid layer or the solid pastilles or prills are removed from the plane as is customary and bottled, the thin layers usually being comminuted to a desired flake size by breakage. The production process of flakes, pastilles and prills can take place discontinuously (batch process) or continuously, where, in a continuous method, a continuously circulating steel belt, for example, can be used as mold for the purposes of the present invention.

The present invention further provides a method for the production of pourable or flowable particles of crystalline n-hexyl 2-(4-N,N-diethylamino-2-hydroxybenzoyl)benzoate having an average particle diameter of from 10 μm to 22 cm, comprising the steps a') providing a clear melt of n-hexyl 2-(4-N,N-diethylamino-2-hydroxybenzoyl)benzoate at a temperature above 57° C., b') stirring the melt from process step a') at a temperature below 57° C. until opacity arises, c') transferring the opaque melt to a mold, d') crystallizing out the transferred melt of n-hexyl 2-(4-N,N-diethylamino-2-hydroxybenzoyl)benzoate at a temperature below 57° C. in the mold, e') removing the crystallized-out n-hexyl 2-(4-N,N-diethylamino-2-hydroxybenzoyl)benzoate from the mold and optionally f') comminuting the crystalline n-hexyl 2-(4-N,N-diethylamino-2-hydroxybenzoyl)benzoate from process step e') to the desired particle size.

By the method according to the invention it is possible to produce pourable or flowable particles of crystalline n-hexyl 2-(4-N,N-diethylamino-2-hydroxybenzoyl)benzoate with an average particle diameter of from 10 μm to 22 cm.

The size of the particles can be adjusted as required through the choice of mold into which the opaque melt is transferred, or through a further comminution step. Preferably, particles of crystalline n-hexyl 2-(4-N,N-diethylamino-2-hydroxybenzoyl)benzoate with an average particle diameter of from 0.1 to 5 mm are produced by the method according to the invention.

As already described above, the n-hexyl 2-(4-N,N-diethylamino-2-hydroxybenzoyl)benzoate can, owing to its origin, also comprise small amounts of impurities from the synthesis, such as starting materials, intermediates, by-products and/or solvents.

The content of n-hexyl 2-(4-N,N-diethylamino-2-hydroxybenzoyl)benzoate in the melt provided in process step a') is preferably at least 90% by weight, particularly preferably at least 95% by weight, in particular at least 98% by weight.

Accordingly, preference is given to a method according to the invention in which the melt of n-hexyl 2-(4-N,N-diethylamino-2-hydroxybenzoyl)benzoate in process step a') has a purity of at least 98% by weight, preferably at least 98.5% by weight, in particular at least 99% by weight.

In process step b') of the method according to the invention, the melt from process step a') is stirred at a temperature below 57° C. until opacity arises. Preferably, process step b') is carried out at a temperature between 25 and 40° C., particularly preferably at a temperature between 27 and 35° C.

With regard to the stirrers and stirring conditions that can be used in process step b'), and also preferred embodiments, reference is made to the statements above.

The opacity which arises can be perceived visually by close inspection or else also be ascertained by means of one or more suitable measuring cells located in the melt. It has also been established that the appearance of the opacity is accompanied by a slowing in the cooling rate as far as a slight temperature increase without input of external energy caused by the release of heat of crystallization. In the experiments, it was found that upon reaching such a temperature state of the melt, the latter was opaque, could still be transferred without problems to a mold and then, at the latest after 2 days, was completely crystallized through.

In process step c'), the opaque melt is transferred to a mold, where in principle the geometry and the construction of the mold are unimportant. However, preference is given to using those molds for which removal of the solid, crystallized-out ester presents no difficulties. Conical molds have proven to be advantageous. The volume of the molds is in principle arbitrary and can vary, for example, from 0.1 ml to 10 l or else 5 l to 100 l. The plane surfaces described above are likewise advantageous as mold from which the ester can likewise be separated off without problems after it has crystallized out.

In process step d'), the melt of n-hexyl 2-(4-N,N-diethylamino-2-hydroxybenzoyl)benzoate transferred to the mold or placed onto the plane surface as mold is left to crystallize out at a temperature below 57° C. Preferably, the melt is left to crystallize out at a temperature of from 15 to 35° C.

In process step e'), the crystallized-out n-hexyl 2-(4-N,N-diethylamino-2-hydroxybenzoyl)benzoate is removed from the mold and optionally the crystalline n-hexyl 2-(4-N,N-diethylamino-2-hydroxybenzoyl)benzoate is comminuted to the desired particle size. Preference is given to a method in which the solidified product from process step e') is comminuted, preferably to an average particle size of from 0.1 to 5 mm. If, in process step c'), a plane surface has been used as mold for the purposes of the present invention, for example a steel belt, then the product which is produced in layers can, following separation from the plane surface, be comminuted by breakage, whereas the product which is produced directly in the desired size as pastilles or prills is usually not further comminuted following separation from the plane surface.

The comminution step f') can be carried out by various means or in suitable devices. Preferably, the comminution step is carried out in a mill, the choice of mill being governed by the desired degree of comminution.

The present invention further provides pourable or flowable particles of crystalline n-hexyl 2-(4-N,N-diethylamino-2-hydroxybenzoyl)benzoate having an average particle diameter of from 0.1 to 5 mm, a bulk density greater than 0.35 g/ml, preferably greater than 0.4 g/ml, in particular greater than 0.5 g/ml and a purity of at least 98% by weight, preferably at least 98.5% by weight, in particular of at least 99% by weight.

The present invention also relates to the use of the above-described pourable or flowable particles of crystalline n-hexyl 2-(4-N,N-diethylamino-2-hydroxybenzoyl)benzoate with an average particle diameter of from 0.1 to 5 mm, a bulk density greater than 0.35 g/ml, preferably greater than 0.4 g/ml, in particular greater than 0.5 g/ml and a purity of at least 98% by weight, preferably at least 98.5% by weight, in particular of at least 99% by weight, as UV filter or as free-radical scavenger in cosmetic and dermatological preparations or as product protection.

The advantage of the method according to the invention is based on the fact that it is possible to produce the crystalline n-hexyl 2-(4-N,N-diethylamino-2-hydroxybenzoyl)benzoate in a reproducible and time-saving manner starting from a metastable melt of the high-purity ester. The pourable or flowable particles of crystalline n-hexyl 2-(4-N,N-diethylamino-2-hydroxybenzoyl)benzoate according to the invention represent a nondusting form of the ester which can be incorporated without problems into cosmetic preparations.

The invention is explained by the following, but non-invention-limiting examples.

The melting point of the n-hexyl 2-(4-N,N-diethylamino-2-hydroxybenzoyl)benzoate used was measured in accordance with Ph.Eur. (European Pharmacopoeia 5.0). A value of 57° C. was determined as melting point.

EXPERIMENTS FOR CONTROLLED CRYSTALLIZATION

Example 1—Comparative Example 5 kg of molten n-hexyl 2-(4-N,N-diethylamino-2-hydroxybenzoyl)benzoate with a purity of more than 99% were allowed to cool at room temperature and stand in order to achieve crystallization of the substance. First crystals were observed after 10 days. After 2 months, the entire mass of the ester had crystallized.

Example 2—Comparative Example

At about 40° C., 100 g of fine crystals of n-hexyl 2-(4-N, N-diethylamino-2-hydroxybenzoyl)benzoate (<100 µm) were added to 5 kg of molten n-hexyl 2-(4-N,N-diethylamino-2-hydroxybenzoyl)benzoate. The melt was then left to cool to room temperature. First crystals were observed after 10 days. After 2 months, the entire mass of the ester had crystallized.

Example 3—Comparative Example 5 kg of molten n-hexyl 2-(4-N,N-diethylamino-2-hydroxybenzoyl)benzoate was allowed to cool to 5° C. and stand at this temperature in order to achieve crystallization of the substance. First crystals were observed after 10 days. After 2 months at 5° C., the entire mass of the ester had crystallized.

Example 4—Comparative Example

At about 40° C., 100 g of fine crystals of n-hexyl 2-(4-N, N-diethylamino-2-hydroxybenzoyl)benzoate (<100 µm) were added to 5 kg of molten n-hexyl 2-(4-N,N-diethylamino-2-hydroxybenzoyl)benzoate. The melt was then left to cool to room temperature. First crystals were observed after 10 days. After 2 months, the entire mass of the ester had crystallized.

Example 5 (According to the Invention)

5 kg of molten n-hexyl 2-(4-N,N-diethylamino-2-hydroxybenzoyl)benzoate were transferred to a 5 l aluminum container, Using a magnetic stirrer rod (40 mm), the melt, cooling to room temperature, was stirred for 4 hours at 80 rpm. After 4 hours, first crystals were observed. Complete crystallization took place within 14 days.

Example 6 (According to the Invention)

5 kg of molten n-hexyl 2-(4-N,N-diethylamino-2-hydroxybenzoyl)benzoate were transferred to a 5 l aluminum container. The melt was stirred with a PTFE propeller stirrer (60 mm diameter), which was driven by an electric motor at a stirring speed of 250 rpm at room temperature. After the melt had been stirred for 11 hours, the viscosity of the melt had increased so much that stirring could not be continued. First crystals appeared after stirring for five hours and complete crystallization took place within 24 hours.

Example 7 (According to the Invention)

800 g of molten n-hexyl 2-(4-N,N-diethylamino-2-hydroxybenzoyl)benzoate were transferred to a 1 l glass jacketed reactor (HWS). The temperature of the melt was 60° C. The melt was stirred using a PTFE blade stirrer (75 mm diameter) for 6 hours with a stirring speed of 350 rpm. First crystals were observed after 4 hours and the temperature of the melt at this time was about 33° C. This temperature of the melt remained constant for some time. After 6 hours, a very opaque melt was observed, the temperature of which was 33° C. This opaque, viscous melt was transferred from the reactor to an aluminum crystallization container. Complete crystallization took place within 24 hours.

Example 8 (According to the Invention)

800 g of molten n-hexyl 2-(4-N,N-diethylamino-2-hydroxybenzoyl)benzoate were transferred to a 1 l glass jacketed reactor (HWS), and the melt was stirred using a PTFE blade stirrer (75 mm diameter) with a stirring speed of 250 rpm. After 2 hours, the melt had a temperature, which remained constant, of 28° C. The cloud point of the melt was achieved after stirring for twelve hours. Complete crystallization of the ester took place within 24 hours.

Example 9 (According to the Invention)

1000 g of molten n-hexyl 2-(4-N,N-diethylamino-2-hydroxybenzoyl)benzoate were transferred, as 60° C. warm melt, to a 1 l glass jacketed reactor (HWS). The melt cooled without stirring over the course of 2 hours to a temperature of 32° C. The melt was then stored for 18 hours without stirring and themostated at 35° C. The thermostating was switched off and the melt was stirred using a PTFE propeller stirrer (60 mm diameter) for 30 minutes at a stirring speed of 350 rpm. After stirring for ten minutes, the temperature of the melt was 33° C. After stirring for thirty minutes, the temperature of the melt was 33.5° C. The melt became opaque and first crystals were evident. The melt was then transferred to an aluminum mold. Complete crystallization of the ester took place within 4 hours.

Experiments for Grinding

Example 10 (According to the Invention)

100 g of crystalline n-hexyl 2-(4-N,N-diethylamino-2-hydroxybenzoyl)benzoate from example 9 were comminuted in an attrition mill (Alexander grater in food mode with a 3-blade rotor from Alexanderwerk Remscheid) with a sieve of mesh width 4.0×7.5 mm, 71.2% of the comminuted material had a particle size in the range of from 0.5 to 5 mm. The fines fraction with a particle size of less than 100 μm had a content of 2.5% by weight. This fines fraction was determined by sieving.

The invention claimed is:

1. A method for the crystallization of n-hexyl 2-(4-N,N-diethylamino-2-hydroxybenzoyl)benzoate comprising the steps
    a) providing a clear melt of n-hexyl 2-(4-N,N-diethylamino-2-hydroxybenzoyl)-benzoate at a temperature above 57° C., and
    b) crystallizing out n-hexyl 2-(4-N,N-diethylamino-2-hydroxybenzoyl)benzoate at a temperature below 57° C.,
    wherein the clear melt from process step a) is stirred at a temperature below 57° C. until opacity arises, before process step b) is carried out and wherein the n-hexyl 2-(4-N,N-diethylamino-2-hydroxybenzoyl)benzoate has an average particle diameter of from 0.1 to 5 mm and a bulk density greater than 0.35 g/ml.

2. The method according to claim 1, wherein the melt of n-hexyl 2-(4-N,N-diethylamino-2-hydroxybenzoyl)benzoate in process step a) has a purity of at least 98% by weight.

3. The method according to claim 1, wherein the melt prepared in process step a) is stirred at a temperature between 25 and 40° C. until opaque.

4. The method according to claim 2, wherein the melt prepared in process step a) is stirred at a temperature between 27 and 35° C. until opaque.

5. The method according to claim 1, wherein process step b) is carried out at a temperature of from 15 to 35° C.

6. The method according to claim 4, wherein process step b) is carried out at a temperature of from 15 to 35° C.

7. The method according to claim 1, wherein the melt is stirred with a stirrer which has a diameter of from 2 to 20 cm at 200 to 500 rpm.

8. The method according to claim 6, wherein the melt is stirred with a stirrer which has a diameter of from 2 to 20 cm at 300 to 400 rpm.

9. A method for the production of pourable or flowable particles of crystalline n-hexyl 2-(4-N,N-diethylamino-2-hydroxybenzoyl)benzoate having an average particle diameter of from 10 μm to 22 cm comprising the steps
    a') providing a clear melt of n-hexyl 2-(4-N,N-diethylamino-2-hydroxybenzoyl)-benzoate at a temperature above 57° C.,
    b') stirring the melt from process step a') at a temperature below 57° C. until opacity arises,
    c') transferring the opaque melt to a mold,
    d') crystallizing out the transferred melt of n-hexyl 2-(4-N,N-diethylamino-2-hydroxybenzoyl)benzoate at a temperature below 57° C. in the mold,
    e') removing the crystallized-out n-hexyl 2-(4-N,N-diethylamino-2-hydroxybenzoyl)benzoate from the mold and optionally
    f') comminuting the crystalline n-hexyl 2-(4-N,N-diethylamino-2-hydroxybenzoyl)benzoate from process step e') to the desired particle size.

10. The method according to claim 9, wherein the melt of n-hexyl 2-(4-N,N-diethylamino-2-hydroxybenzoyl)benzoate in process step a') has a purity of at least 98% by weight.

11. The method according to claim 9, wherein process step b') is carried out at a temperature between 25 and 40° C.

12. The method according to claim 10, wherein process step b') is carried out at a temperature between 27 and 35° C.

13. The method according to claim 9, wherein process step d') is carried out at a temperature of from 15 to 35° C.

14. The method according to claim 12, wherein process step d') is carried out at a temperature of from 15 to 35° C.

15. The method as claimed in claim 1, wherein the amount n-hexyl 2-(4-N,N-diethylamino-2-hydroxybenzoyl)-benzoate in the melt is at least 90% by weight.

16. The method as claimed in claim 1, wherein the amount n-hexyl 2-(4-N,N-diethylamino-2-hydroxybenzoyl)-benzoate in the melt is at least 98% by weight.

* * * * *